(12) United States Patent
Coulthard et al.

(10) Patent No.: US 9,877,873 B2
(45) Date of Patent: *Jan. 30, 2018

(54) EVAPORATIVE FLUID POUCH AND SYSTEMS FOR USE WITH BODY FLUIDS

(71) Applicant: KCI Licensing, Inc., San Antonio, TX (US)

(72) Inventors: Richard Daniel John Coulthard, Verwood (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 210 days.

This patent is subject to a terminal disclaimer.

(21) Appl. No.: 14/860,165

(22) Filed: Sep. 21, 2015

(65) Prior Publication Data

US 2016/0058925 A1    Mar. 3, 2016

Related U.S. Application Data

(63) Continuation of application No. 13/442,567, filed on Apr. 9, 2012, now Pat. No. 9,314,377, which is a
(Continued)

(51) Int. Cl.
*A61M 1/00* (2006.01)
*A61F 13/00* (2006.01)
(Continued)

(52) U.S. Cl.
CPC .... *A61F 13/00055* (2013.01); *A61F 13/0216* (2013.01); *A61M 1/009* (2014.02);
(Continued)

(58) Field of Classification Search
CPC .......... A61M 1/00; A61M 5/178; A61M 5/00; A61M 5/32; A61M 35/00; A61F 13/00
See application file for complete search history.

(56) References Cited

U.S. PATENT DOCUMENTS 1,355,846 A    10/1920  Rannells
2,547,758 A    4/1951   Kelling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Tatyana Zalukaeva
*Assistant Examiner* — Ilya Treyger

(57) ABSTRACT

An inline storage-and-liquid-processing pouch for use with body fluids from a patient is presented that involves introducing body fluids into a first chamber in the storage-and-liquid-processing pouch and flowing air through a second chamber. The chambers are separated by a high-moisture-vapor-transfer-rate member. The air flow in the second chamber enhances liquid removal from the first chamber across the high-moisture-vapor-transfer-rate member. Other systems, devices, and methods are disclosed herein.

22 Claims, 5 Drawing Sheets

Related U.S. Application Data continuation-in-part of application No. 13/084,813, filed on Apr. 12, 2011, now Pat. No. 8,604,265.

(60) Provisional application No. 61/529,709, filed on Aug. 31, 2011, provisional application No. 61/529,722, filed on Aug. 31, 2011, provisional application No. 61/529,735, filed on Aug. 31, 2011, provisional application No. 61/529,751, filed on Aug. 31, 2011.

(51) Int. Cl.
    *A61F 13/02*     (2006.01)
    *A61M 27/00*     (2006.01)
    *A61M 5/178*     (2006.01)
    *A61M 5/00*     (2006.01)
    *A61M 5/32*     (2006.01)
    *A61M 35/00*     (2006.01)

(52) U.S. Cl.
    CPC ........ *A61M 1/0023* (2013.01); *A61M 1/0058* (2013.01); *A61M 27/00* (2013.01); *Y10T 29/49826* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |

(56) References Cited

FOREIGN PATENT DOCUMENTS

| WO | 94/020041 A1 | 9/1994 |
|---|---|---|
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, YU. A., et al; "Vacuum Therapy in the Treatment of Purulent Lactation Mastitis"; Vestnik Khirurgi, May 14, 1986, pp. 66-70, and 9 page English translation thereof.
Yusupov. YU.N., et al; "Active Wound Drainage", Vestnki Khirurgi, vol. 138, Issue 4, 1987, and 7 page English translation thereof.
Davydov, YU.A., et al; "Bacteriological and Cytological Assessment of Vacuum Therapy for Purulent Wounds"; Vestnik Khirugi, Oct. 1988, pp. 48-52, and 8 page English translation thereof.
Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

EVAPORATIVE FLUID POUCH AND SYSTEMS FOR USE WITH BODY FLUIDS

RELATED APPLICATIONS

The present invention is a continuation of U.S. patent application Ser. No. 13/442,567 filed Apr. 9, 2012; which is a continuation-in-part of U.S. patent application Ser. No. 13/084,813, entitled "DRESSINGS AND METHODS FOR TREATING A TISSUE SITE ON A PATIENT," filed on 12 Apr. 2011, now U.S. Pat. No. 8,604,265 and incorporated herein by reference; and which claims the benefit, under 35 USC §119(e), of the filings of: U.S. Provisional Patent Application Ser. No. 61/529,709, entitled "EVAPORATIVE FLUID POUCH AND SYSTEMS FOR USE WITH BODY FLUIDS," filed 31 Aug. 2011, which is incorporated herein by reference for all purposes; U.S. Provisional Patent Application Ser. No. 61/529,722, entitled "REDUCED-PRESSURE DRESSINGS, SYSTEMS, AND METHODS WITH EVAPORATIVE DEVICES," filed on 31 Aug. 2011, which is incorporated herein by reference for all purposes; U.S. Provisional Patent Application Ser. No. 61/529,735, entitled "ABSORBENT POLYMER DRESSINGS, SYSTEMS, AND METHODS EMPLOYING EVAPORATIVE DEVICES," filed 31 Aug. 2011, which is incorporated herein by reference for all purposes; and U.S. Provisional Patent Application Ser. No. 61/529,751, entitled "REDUCED-PRESSURE INTERFACES, SYSTEMS, AND METHODS EMPLOYING A COANDA DEVICE," filed on 31 Aug. 2011, which is incorporated herein by reference for all purposes.

FIELD

The present disclosure relates generally to medical treatment systems for treating wounds that produce liquids, such as exudate, and more particularly, but not by way of limitation, to reduced-pressure medical dressings, systems, and methods with evaporative devices.

BACKGROUND

Caring for wounds is important in the healing process. Wounds often produce considerable liquids, e.g., exudate. Medical dressings are often used in wound care to address the production of liquids from the wound. If not properly addressed, liquids at the wound can lead to infection or maceration of the periwound area. As used throughout this document, "or" does not require mutual exclusivity. Wound dressings may be used alone or as an aspect of applying reduced pressure to a tissue site.

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

SUMMARY

According to an illustrative embodiment, an inline storage-and-liquid-processing pouch for use with body fluids from a patient is presented that involves introducing body fluids into a first chamber in the pouch and flowing air through a second chamber where the chambers are separated by a high-moisture-vapor-transfer-rate member. The air flow in the second chamber enhances liquid removal from the first chamber across the high-moisture-vapor-transfer-rate member.

According to another illustrative embodiment, a system for treating a tissue site on a patient with reduced-pressure includes a reduced-pressure dressing for disposing proximate to the tissue site, a first reduced-pressure conduit fluidly coupled to the reduced-pressure dressing for delivery reduced pressure thereto, and an inline storage-and-liquid-processing pouch having a first chamber and a second chamber. The first reduced-pressure conduit is fluidly coupled to the first chamber. The system further includes a reduced-pressure source fluidly coupled to the first chamber and a pressure source fluidly coupled to the second chamber at a first evaporation port. The system also includes a second evaporation port formed on the inline storage-and-liquid-processing pouch. The pressure source is configured to move air within the second chamber.

According to another illustrative embodiment, an inline storage-and-liquid-processing pouch for use with body fluids from a patient includes a pouch body having an interior portion divided into two parts by a first high-moisture-vapor-transfer-rate member to form a first chamber and a second chamber. The inline storage-and-liquid-processing pouch also includes a storage material disposed within the first chamber and an air-movement manifold disposed within the second chamber. The inline storage-and-liquid-processing pouch also includes a first port formed on the pouch body and fluidly coupled to the first chamber; a second port formed on the pouch body and fluidly coupled to the first chamber; a first evaporation port formed on the pouch body and fluidly coupled to the second chamber; and a second evaporation port formed on the pouch body and fluidly coupled to the second chamber.

According to another illustrative embodiment, a method for temporarily storing and processing body fluids outside of a patient includes providing an inline storage-and-liquid-processing pouch. The inline storage-and-liquid-processing pouch includes a pouch body having an interior portion divided into two parts by a first high-moisture-vapor-transfer-rate member to form a first chamber and a second chamber. The inline storage-and-liquid-processing pouch further includes a storage material disposed within the first chamber and an air-movement manifold disposed within the second chamber. The inline storage-and-liquid-processing pouch further includes a first port formed on the pouch body and fluidly coupled to the first chamber; a second port formed on the pouch body and fluidly coupled to the first chamber; a first evaporation port formed on the pouch body and fluidly coupled to the second chamber; and a second evaporation port formed on the pouch body and fluidly coupled to the second chamber. The method further includes delivering the body fluids, which include liquids, to the first port and into the first chamber and developing an airflow in the second chamber through the air-movement manifold. As a result, a humidity gradient is maintained across the first high-moisture-vapor-transfer-rate member to evaporate liquids from the first chamber.

According to still another illustrative embodiment, an inline storage-and-liquid-processing pouch for use with body fluids from a patient includes a pouch body having an interior portion divided into three parts by a first high-moisture-vapor-transfer-rate member and a second high-moisture-vapor-transfer-rate member to form a first chamber, a second chamber, and a third chamber. The first chamber is between the second and third chambers. The inline storage-and-liquid-processing pouch further includes a storage material disposed within the first chamber, a first air-movement manifold disposed within the second chamber, and a second air-movement manifold disposed within the second chamber. The inline storage-and-liquid-processing pouch also includes a first port formed on the pouch body and fluidly coupled to the first chamber; a second port formed on the pouch body and fluidly coupled to the first chamber; a first evaporation port formed on the pouch body and fluidly coupled to the second chamber; a second evaporation port formed on the pouch body and fluidly coupled to the second chamber; a third evaporation port formed on the pouch body and fluidly coupled to the third chamber; and a fourth evaporation port formed on the pouch body and fluidly coupled to the third chamber proximate to the second end.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Figure 1:
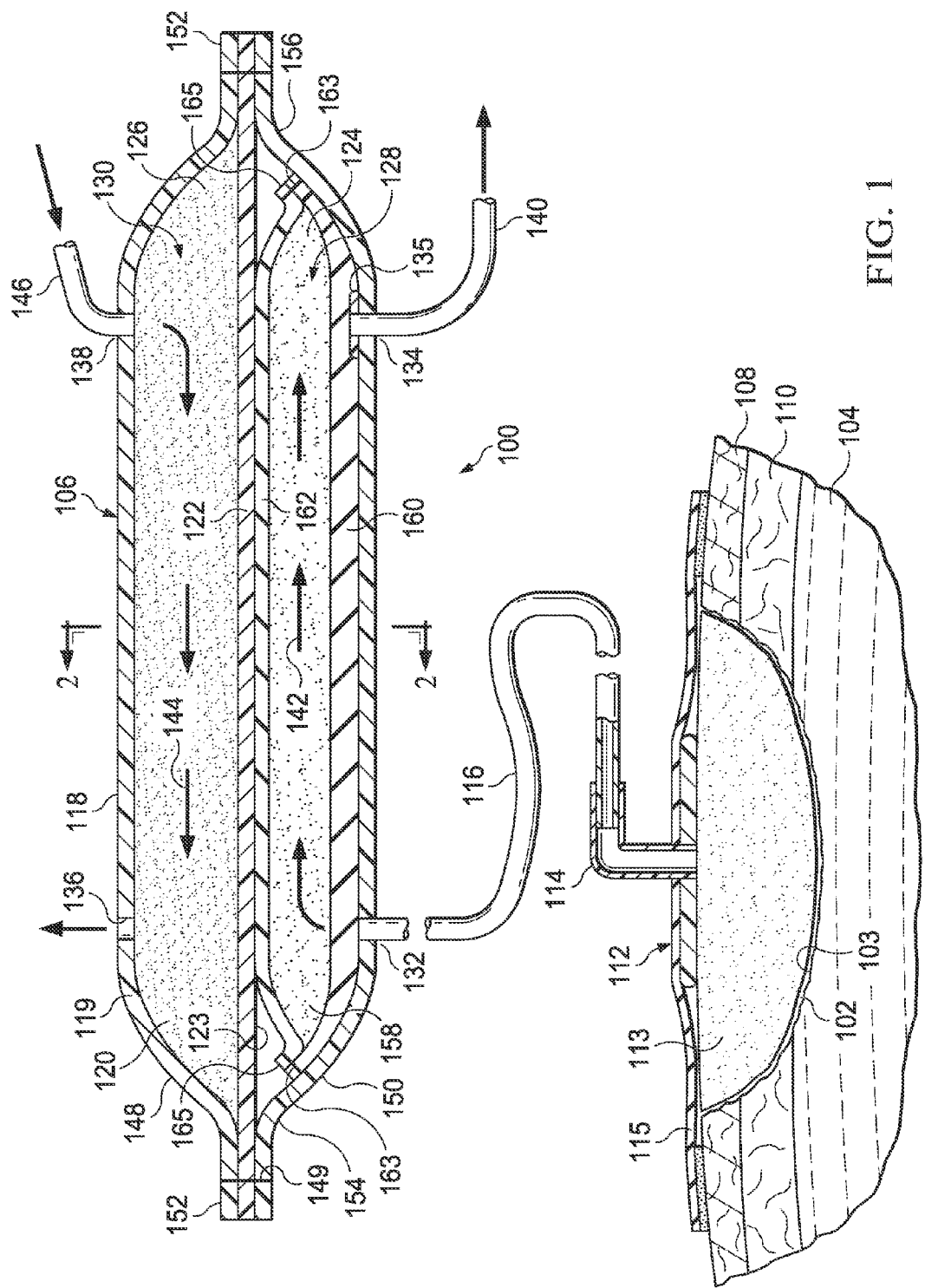
FIG. 1 is a schematic, cross sectional view of an illustrative embodiment of a system for treating a tissue site on a patient with reduced pressure that includes an inline storage-and-liquid-processing pouch.
Figure 2:
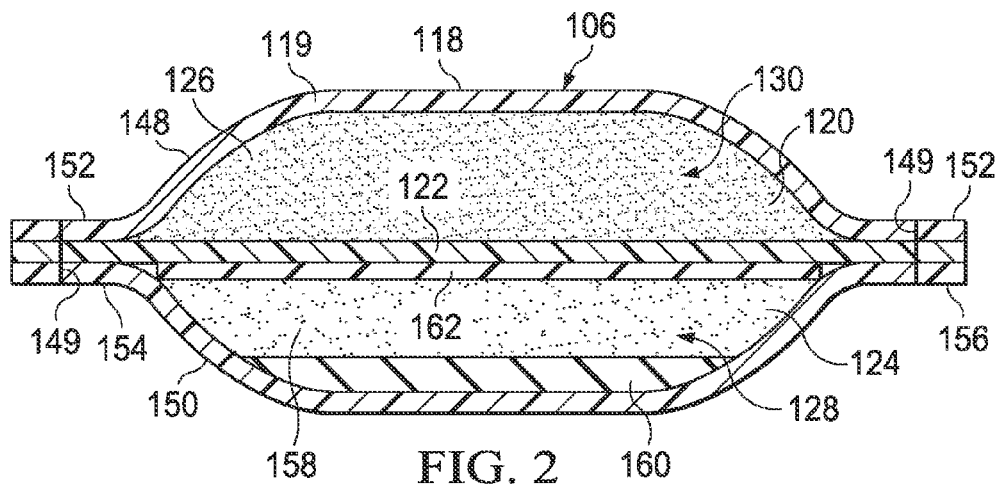
FIG. 2 is a schematic, lateral cross sectional view of the inline storage-and-liquid-processing pouch of FIG. 1 taken along line 2-2 and made into a whole cross section.

Referring now to the figures and primarily to FIG. 1-2, a system 100 for treating a tissue site 102, such as a wound 103, on a patient 104 with reduced-pressure is presented. The system 100 includes an illustrative embodiment of an inline storage-and-liquid-processing pouch 106 that allows the system 100 to process more liquids from the tissue site 102 than would otherwise be possible as well as offering other potential benefits.

The depicted wound 103 at tissue site 102 is through epidermis 108 and into dermis 110. A reduced-pressure dressing 112 is disposed on the tissue site 102 and is operable to receive fluids from the tissue site 102. The reduced-pressure dressing 112 may be any type of dressing for receiving fluids from the patient, but is shown as a dressing with a wound-interface manifold 113 and a drape 115. Indeed, the reduced-pressure dressing 112 may involve only removing fluids from a body-fluid container, such as an ostomy bag. Fluids, including liquids, from the tissue site 102 are delivered through a reduced-pressure interface 114 to a first reduced-pressure conduit 116 that is fluidly coupled to the inline storage-and-liquid-processing pouch 106.

As an overview of the illustrative embodiment of the inline storage-and-liquid-processing pouch 106, the inline storage-and-liquid-processing pouch 106 includes a pouch body 118 formed with exterior walls 119 and having an interior portion 120 that divided into two parts by a first high-moisture-vapor-transfer-rate member 122. The exterior walls 119 and first high-moisture-vapor-transfer-rate member 122 form a first chamber 124 and a second chamber 126. A storage material 128 is disposed within the first chamber 124. An air-movement manifold 130 is disposed in the second chamber 126. These aspects of the inline storage-and-liquid-processing pouch 106 and others will be further described.

A first port 132 is formed on the pouch body 118 and fluidly coupled to the first chamber 124. A second port 134 is formed on the pouch body 118 and fluidly coupled to the first chamber 124. A first evaporation port 136 is formed on the pouch body 118 and is fluidly coupled to the second chamber 126. A second evaporation port 138 is formed on the pouch body 118 and fluidly coupled to the second chamber 126. Reduced pressure is applied to the second port directly by a reduced-pressure source, e.g., a micro-pump (see FIG. 4), or by a second reduced-pressure conduit 140 (FIG. 1). The first evaporation port 136, which is the outlet to the second chamber 126, may have a bacteria filter over the first evaporation port 136 to filter the air before the air exits the second chamber 126.

Thus, liquids are pulled into the first chamber 124 as suggested by arrows 142 from the reduced-pressure dressing 112. A hydrophobic filter 135 or other device may be placed at the downstream port, i.e., the second port 134 in FIG. 1, to prevent liquids from exiting through the downstream port. As suggested by arrows 144, air is caused to flow in the second chamber 126 that helps create or maintain a relative humidity gradient across the first high-moisture-vapor-transfer-rate member 122 and that helps remove liquids from the inline storage-and-liquid-processing pouch 106 and more generally the system 100. While air is mentioned throughout this document, it should be understood that another working gas could be used and that air is being used in a broad sense to reference a gas that creates the humidity gradient across the first high-moisture-vapor-transfer-rate member 122.

The first high-moisture-vapor-transfer-rate member 122 may be formed from any material that allows vapor to egress but not liquids. "Moisture Vapor Transmission Rate" or "MVTR" represents the amount of moisture that can pass through a material in a given period of time. The first high-moisture-vapor-transfer-rate member 122 typically has a moisture vapor transmission rate greater than 300 g/m$^2$/24 hours and more typically 1000 g/m²/24 hours or more. The first high-moisture-vapor-transfer-rate member 122 allows vapor to egress or diffuse from the first chamber 124 to the second chamber 126, but not liquids.

The first high-moisture-vapor-transfer-rate member 122 may comprise one or more of the following: hydrophilic polyurethane, cellulosics, hydrophilic polyamides, an INSPIRE 2301 material from Exopack Advanced Coatings of Wrexham, United Kingdom; a thin, uncoated polymer drape; or polyvinyl alcohol, polyvinyl pyrrolidone, hydrophilic acrylics, hydrophilic silicone elastomers and copolymers of these. The INSPIRE 2301 illustrative film has an MVTR (inverted cup technique) of 14500-14600 g/m²/24 hours. See www.exopackadvancedcoatings.com. The first high-moisture-vapor-transfer-rate member 122 may have various thicknesses, such as 10 to 40 microns (μm), e.g., 15, 20, 25, 30, 35, 40 microns (inclusive of all numbers in the stated range).

A patient-facing side 123 of the first high-moisture-vapor-transfer-rate member 122 may be coupled by an attachment device (not shown), e.g., adhesive or cement, to the top side (for the orientation shown in FIG. 1) of the storage material 128, e.g., top of the second wicking member 162. In such an embodiment, the performance of the first high-moisture-vapor-transfer-rate member 122 with respect to MVTR may be enhanced by only covering a limited surface area of the patient-facing side 123 with the attachment device. For example, according to one illustrative embodiment, only 30 to 60 percent of the surface area of the patient-facing side 123 is covered with the attachment device. The limited coverage by the attachment device on the patient-facing side 123 may be accomplished by applying the attachment device in a pattern, e.g., grid, spaced dots, swirls, or other patterns. In another embodiment, the first high-moisture-vapor-transfer-rate member 122 may be coupled by welding (e.g., ultrasonic or RF welding), bonding, stitching, staples, or another coupling device to the storage material 128. In other embodiments, there is no attachment device.

The air flow in the second chamber 126 may be achieved in either direction and is shown in FIG. 1 flowing in a direction opposite the reduced pressure flow of the first chamber 124. In the embodiment shown, a positive pressure is applied to the second evaporation port 138. The positive pressure may be applied directly by a micro-pump or other device (see FIG. 4) or by positive pressure delivered by a pressure conduit 146. When configured to apply positive pressure to the second evaporation port 138, the first evaporation port 136 functions as an outlet for flowing air to exit the second chamber 126. Alternatively, reduced pressure may be applied either directly or through pressure conduit 146 to the second evaporation port 138. In that instance, the first evaporation port 136 functions as an intake for allowing air to enter the second chamber 126.

The pouch body 118 may be formed in numerous ways. According to one illustrative embodiment, the exterior walls 119 are formed by a first sealing member 148 and a second sealing member 150. The first sealing member 148 is bonded by bond 149 to the second sealing member 150 at peripheral ends 152. The first high-moisture-vapor-transfer-rate member 122 is disposed between the first sealing member 148 and second sealing member 150 and may be bonded with bonds 149 as well. The first high-moisture-vapor-transfer-rate member 122 thereby forms two parts or bisects (not necessarily equal parts) the interior portion 120 to form the first chamber 124 and the second chamber 126.

The first sealing member 148 is formed from any material that inhibits air flow through the first sealing member 148 and typically that is liquid impermeable as well. In some embodiments, the first sealing member 148 may be a high-moisture-vapor-transfer-rate material to allow additional liquid to egress the second chamber 126. The second sealing member 150 is formed from any liquid-impermeable material. Typically, the first sealing member 148 and second sealing member 150 are formed from one or more of the following: natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, silicones, silicone drape, a 3M Tegaderm® drape, or a polyurethane (PU) drape such as one available from Avery Dennison Corporation of Pasadena, Calif., or any material mentioned for the first high-moisture-vapor-transfer-rate member 122, or other appropriate material. The first sealing member 148 need not be liquid impermeable and could also be formed from a woven or non-woven material as long as the material is coated or constructed to contain the air flow.

The ports 132, 134, 136, and 138 are formed through the pouch body 118. Typically, the respective pairs of ports (132 and 132; 136 and 138) are displaced as far as possible from each other to maximize distribution of liquids or evaporation. Thus for example, typically the first port 132 is positioned on a first end 154 of the pouch body 118 and the second port 134 is positioned on the second end 156. Likewise, the first evaporation port 136 is on the first end 154 and the second evaporation port 138 is on the second end 156.

Figure 3:
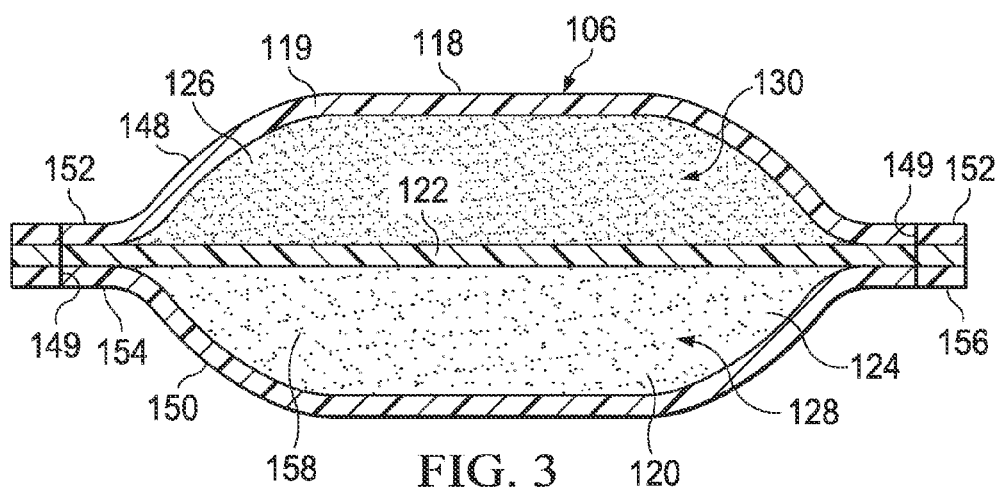
FIG. 3 is a schematic, lateral cross sectional view of an illustrative embodiment of an inline storage-and-liquid-processing pouch.

The storage material 128 is disposed in the first chamber 124. The storage material 128 is any material that receives fluids, including liquids, and retains the fluids. For example, without limitation, the storage material 128 may be formed from one or more of the following: an absorbent member 158, a first wicking member 160, a second wicking member 162. In the illustrative embodiment of FIG. 2, the storage material 128 comprises the absorbent layer 158 and two wicking members 160, 162. In the illustrative embodiment of FIG. 3, the storage material 128 is only an absorbent member 158.

The absorbent member 158 may be any material that retains liquids and may comprise one or more of the following: BASF 402c, Technical Absorbents 2317, sodium polyacrylate super absorbers, cellulosics (carboxy methyl cellulose and salts such as sodium CMC), or alginates. The first wicking member 160 and second wicking member 162 may be formed from one or more of the following: non-woven fabrics such as Libeltex TDL2, woven fabrics including 3D spacer fabrics and Textiles (Baltex, Ilkeston, Derby, UK), open-cell foam, or sintered polymers.

In the illustrative embodiment of FIGS. 1-2, the storage material 128 includes a first wicking member 160, an absorbent member 158, and a second wicking member 162, which is proximate to the first high-moisture-vapor-transfer-rate member 122. The first wicking member 160 and the second wicking member 162 may be coupled at their peripheral edges 165 as shown by a coupling 163. The coupling 163 may be formed using any known technique, including without limitation welding (e.g., ultrasonic or RF welding), bonding, adhesives, cements, stitching, staples, or another coupling device. Alternatively, the first wicking member 160 and the second wicking member 162 may be disposed adjacent to one another at least at their peripheral ends (overlapping portions) and held in contact with one another to allow fluid communication therebetween. The wicking layers 160, 162 may thus be in fluid communication with each other to allow fluid flow between the wicking layers 160, 162 and along the wicking layers 160, 162 at times when the flow of fluid in the absorbent layer 158 is inhibited or blocked.

Figure 4:
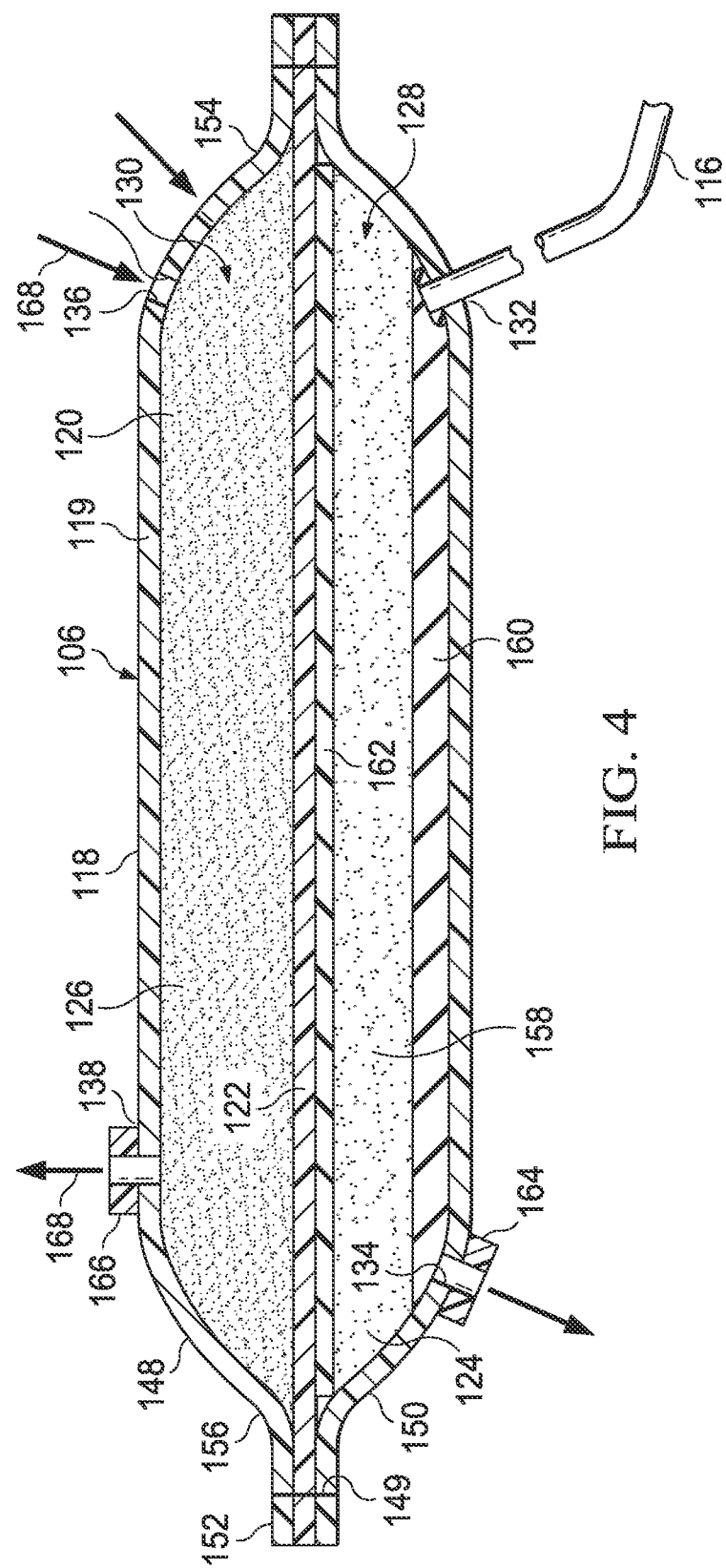
FIG. 4 is a schematic, longitudinal cross sectional view of an illustrative embodiment of an inline storage-and-liquid-processing pouch.

Referring now to FIG. 4, another illustrative embodiment of an inline storage-and-liquid-processing pouch 106 for use with body fluids from a patient is presented. The inline storage-and-liquid-processing pouch 106 is analogous in many respects to the inline storage-and-liquid-processing pouch 106 of FIGS. 1-3, and accordingly, some parts are labeled but not further discussed. The inline storage-and-liquid-processing pouch 106 includes a first micro-pump 164 coupled to the pouch body 118 and fluidly coupled to the second port 134. The first micro-pump 164 is operable to produce reduced pressure that is delivered to the second port 134. The first micro-pump may be any pump capable of producing reduced pressure and small and light weight enough to be attached directly to the pouch body 118. For example, and not by way of limitation, the micro-pump shown in United States Patent Publication 2009/0240185 (application Ser. No. 12/398,904; filed 5 Mar. 2009), entitled, "Dressing and Method for Applying Reduced Pressure To and Collecting And Storing Fluid from a Tissue Site," which is incorporated herein for all purposes, may be used.

Figure 5:
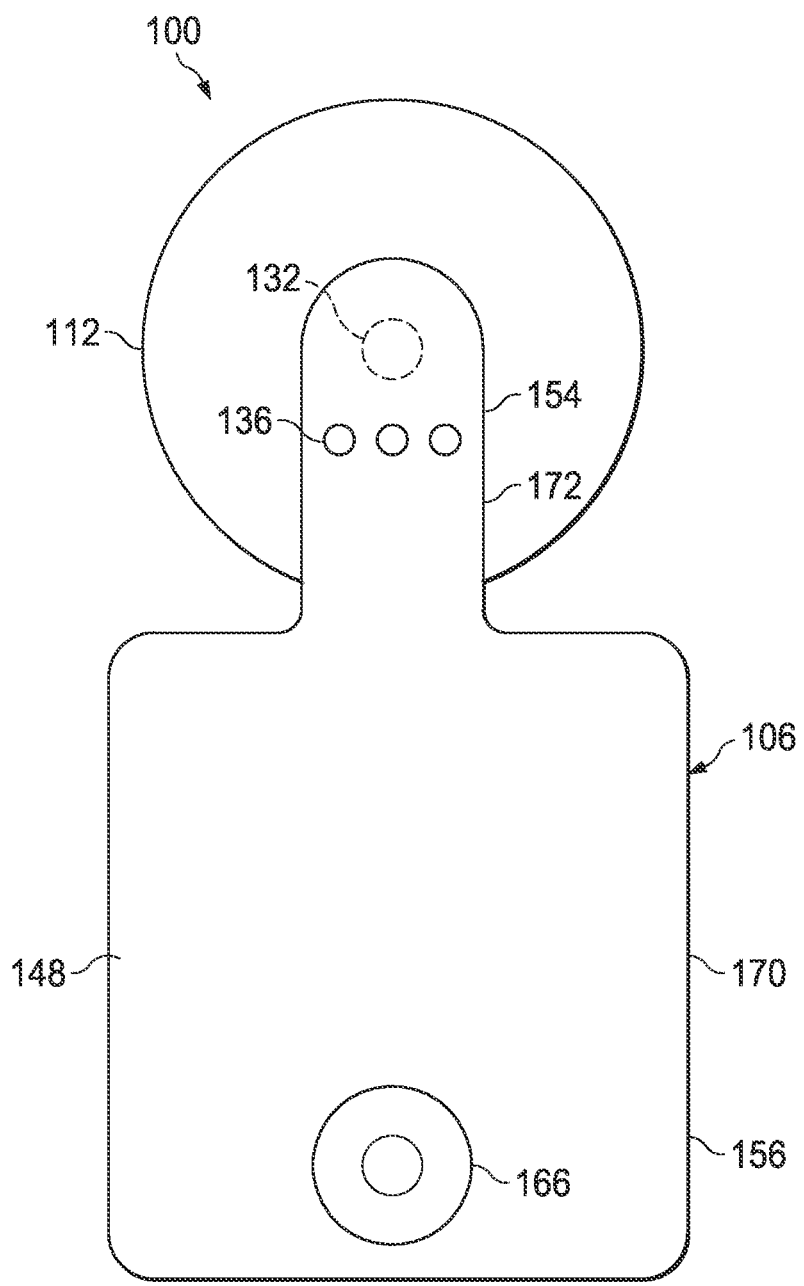
FIG. 5 is a schematic, plan view of an illustrative embodiment of an inline storage-and-liquid-processing pouch.

Similarly, a second micro-pump 166 is coupled to the pouch body 118 and fluidly coupled to the second evaporation port 138. The second micro-pump 166 is operable to produce air flow in the second chamber 126 between the first evaporation port 136 and the second evaporation port 138. The second micro-pump 166 is analogous to the first micro-pump but may configured to either pull air as shown and suggested by arrows 168 or to push air. In the latter situation, air goes from the second evaporation port 138 through the second chamber 126 to the first evaporation port 136. The inline storage-and-liquid-processing pouch 106 may be formed with one or both of the micro-pumps 164, 166 or with one or more conduits 140, 146 as shown in FIG. 1. A first reduced-pressure conduit 116 is fluidly coupled to a wound dressing (not shown), such as the reduced-pressure dressing 112 in FIG. 1, and to the first port 132. As shown in FIG. 5, the reduced-pressure dressing may also be directly coupled to the first port 132.

Referring now primarily to FIG. 5, a plan view of an illustrative system 100 for treating a tissue site on a patient with reduced-pressure that includes an inline storage-and-liquid-processing pouch 106 is presented. The inline storage-and-liquid-processing pouch 106 is analogous in most respects to the inline storage-and-liquid-processing pouch 106 of FIGS. 1-3, and accordingly, some parts are labeled but not further discussed. In addition, components referenced but not explicitly shown are analogous to those previously presented. The embodiment of FIG. 5 differs primarily in that the pouch body 118 has a main portion 170 and a neck portion 172 and the first port 132 is coupled directly to the reduced-pressure dressing 112.

It should be noted that that the inline storage-and-liquid-processing pouch 106 may take many different shapes. Some embodiments of the inline storage-and-liquid-processing pouch 106 are for wearing on the patient and others may be for a stationary position near the patient. In some embodiments, the second chamber 126 may encircle the first chamber 124 or other configurations may be used. The pouch body 118 may take different sizes too. In one illustrative embodiment, the pouch body 118 has surface area in plan view greater than 200 centimeters$^2$ and less than 730 centimeters$^2$.

In the embodiment of FIG. 5, reduced pressure is developed into the first chamber and that reduced pressure pulls liquids from the reduced-pressure dressing 112 directly into the first port 132 and is distributed in the first chamber. A micro-pump 166 pushes or pulls air into the air-movement manifold. Thus, air will enter or exit through the first evaporation port 136, which in this embodiment comprises a plurality of apertures. The movement of air in the second chamber establishes a strong humidity gradient across a first high-moisture-vapor-transfer-rate member and liquid is thus processed out of the system 100.

Figure 6:
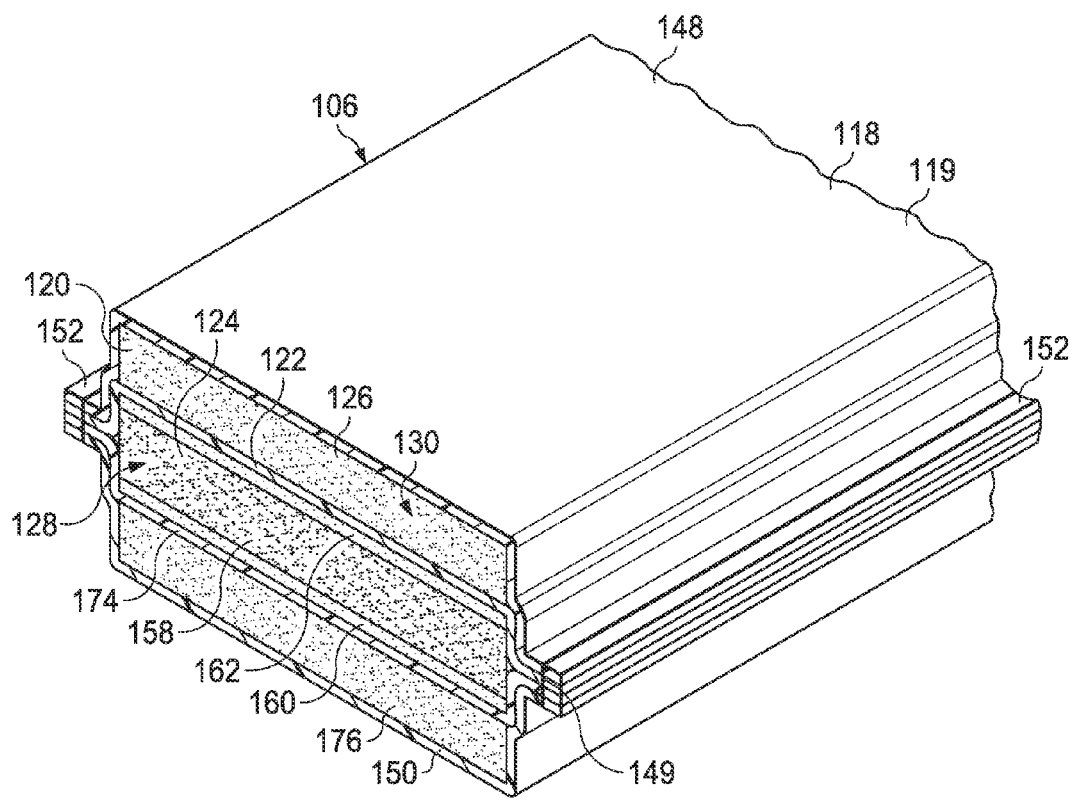
FIG. 6 is a schematic, perspective view, with a portion in cross section (lateral), of an illustrative embodiment of an inline storage-and-liquid-processing pouch.
Figure 7:
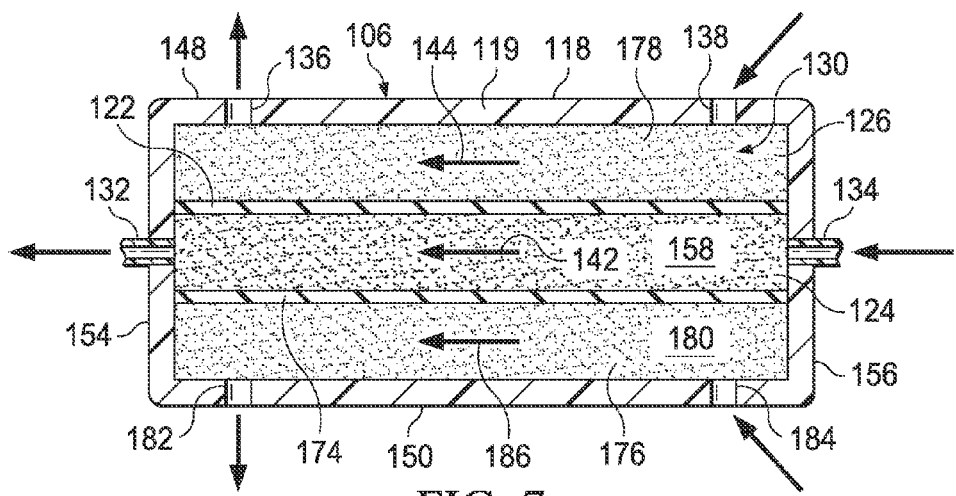
FIG. 7 is a schematic, longitudinal cross sectional view of the inline storage-and-liquid-processing pouch of FIG. 6 with some alterations.

Referring now primarily to FIGS. 6 and 7, another illustrative embodiment of an inline storage-and-liquid-processing pouch 106 is presented. The inline storage-and-liquid-processing pouch 106 is analogous in most respects to the inline storage-and-liquid-processing pouch 106 of FIGS. 1-3, and accordingly, some parts are labeled but not further discussed. In addition, components referenced but not explicitly shown are analogous to those previously presented. This embodiment differs primarily in that three chambers are formed in the interior portion 120 in order to provide for evaporation on two sides of the first chamber 124.

A pouch body 118 is formed having exterior walls 119. The pouch body 118 is partitioned by a first high-moisture-vapor-transfer-rate member 122 and a second high-moisture-vapor-transfer-rate member 174 to form the first chamber 124, a second chamber 126, and a third chamber 176. The second high-moisture-vapor-transfer-rate member 174 may formed from the same materials as the a first high-moisture-vapor-transfer-rate member 122 as previously presented. The first chamber 124 is between the second chamber 126 and third chamber 176. As with previous embodiments, a storage material 128 is disposed within the first chamber 124 and an air-movement manifold 130, which is a first air-movement manifold 178, is disposed within the second chamber 126. In addition, a second air-movement manifold 180 is disposed in the third chamber 176. The first air-movement manifold 178 and second air-movement manifold 180 are formed from one or more of the same materials previously mentioned for the first air-movement manifold 130 in FIGS. 1-3.

The storage material 128 may be any of the materials previously mentioned. FIGS. 6 and 7 differ from one another slightly with respect to the storage material 128. The storage material 128 in FIG. 6 has an absorbent member 158 disposed between a first wicking member 160 and a second wicking member 162. In contrast, the storage material of 128 of FIG. 7 is only an absorbent member 158.

Referring primarily to FIG. 7, a schematic, longitudinal cross section of the inline storage-and-liquid-processing pouch 106 of FIG. 6 is presented. The various ports are shown best in this view. The pouch body 118 is formed with a first port 132 formed on the pouch body 118 and is fluidly coupled to the first chamber 124. A second port 134 is also formed on the pouch body 118 and is fluidly coupled to the first chamber 124. A first evaporation port 136 and a second evaporation port 138 are formed on the pouch body 118 and are fluidly coupled to the second chamber 126. In addition, a third evaporation port 182 is formed on the pouch body 118 and is fluidly coupled to the third chamber 176. Likewise, a fourth evaporation port 184 is formed on the pouch body 118 and is fluidly coupled to the third chamber 176. To maximize distribution or evaporation, the pairs of ports are typically remote from each other and usually one is on the first end 154 and the other on the second end 156.

Referring generally to FIGS. 6 and 7, according to one illustrative embodiment, in operation, the first port 132 is fluidly coupled to the wound dressing (e.g., reduced-pressure dressing 112 in FIG. 1) and receives fluids, including liquid, therefrom. The liquid is pulled through the second port 134 into the first chamber 124 by reduced pressure applied to the first chamber 124 through the first port 132. The liquid is distributed within the storage material 128 from the second port 134 to the first port 132 as suggested by arrows 142. The liquid in the storage material 128 interacts with both the first high-moisture-vapor-transfer-rate member 122 and the second high-moisture-vapor-transfer-rate member 174.

An air flow is produced in the second chamber 126 as suggested by arrows 144. Air may flow to or from the first evaporation port 136 and from or to the second evaporation port 138. The air flow in second chamber 126 is caused by applying positive or reduced pressure to one of the evaporation ports 136, 138. In addition, an air flow is produced in the third chamber 176 as suggested by arrows 186. Air may flow to or from the third evaporation port 182 and from or to the fourth evaporation port 184. The flow in third chamber 176 is caused by applying positive or reduced pressure to one of the evaporation ports 182, 184. In this way, air flowing on both sides of the first chamber 124 enhances the inline storage-and-liquid-processing pouch 106's ability to process liquids out of the inline storage-and-liquid-processing pouch 106.

In all the embodiments herein, the air movement through the second chamber 126 (and third chamber 176 when applicable) may be continuous, intermittent, or actively controlled. In the latter situation, a saturation sensor may be applied in the first chamber 124 or an outward facing side of the high-moisture-vapor-transfer-rate members 122, 174. The saturation sensor may be any device that allows monitoring of the saturation status of the storage material 128. For example, without limitation, the saturation sensor may be a resistive element that changes resistance when liquid covers the sensor, a galvanic cell that creates a voltage when covered with liquid from a wound, a capacitive sensor that changes properties when saturated liquid is nearby, or any other electrical saturation sensor. The saturation sensor is coupled to a controller, and the controller and saturation sensor determine when the storage material 128 or high-moisture-vapor-transfer-rate members 122, 174 are saturated. Upon detecting the same, the controller may activate a pressure source that supplies either reduced pressure or positive pressure to one of the evacuation ports 136, 138. When the saturation sensor and controller determine that the storage material 128 is not saturated, the controller may deactivate the pressure source.

In another illustrative embodiment, an inline storage-and-liquid-processing pouch 106 is coupled directly to a body-fluid bag, e.g., an ostomy bag. The an inline storage-and-liquid-processing pouch 106 may form an outer wall of the fluid-bag itself.

The illustrative systems and inline storage-and-liquid-processing pouches presented herein offer a number of perceived advantages. These include the ability to manage a higher volume of fluid than otherwise possible. In this regard, one may consider that exudate from a wound often has about 88 percent water and 12 percent other materials. With such a device in use, the system may not need changing for a relatively extended period of time. In addition, the inline storage-and-liquid-processing pouch is multi-directional and involves fewer parts than canisters in use. In addition, the inline storage-and-liquid-processing pouch has a low profile and is light. These are only some of the potential advantages.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a tissue site on a patient with reduced-pressure, the system comprising:
   a reduced-pressure dressing for disposing proximate to the tissue site;
   a first reduced-pressure conduit fluidly coupled to the reduced-pressure dressing for delivery of reduced pressure thereto; and
   an inline storage-and-liquid-processing pouch having a first chamber and a second chamber, wherein the first chamber is fluidly coupled to the first reduced-pressure conduit and configured to be fluidly coupled to a reduced-pressure source, and wherein the second chamber has an evaporation port adapted to allow air to flow out of the second chamber and is configured to be fluidly coupled to a positive-pressure source.

2. The system of claim 1, wherein the inline storage-and-liquid-processing pouch comprises:
   a pouch body having an interior portion divided into two parts by a first high-moisture-vapor-transfer-rate member to form the first chamber and the second chamber;
   a storage material disposed within the first chamber; and
   an air-movement manifold disposed within the second chamber.

3. The system of claim 2, wherein the storage material comprises an absorbent member.

4. The system of claim 2, wherein the storage material comprises an absorbent member and a first wicking member.

5. The system of claim 2, wherein the storage material comprises an absorbent member, a first wicking member, and a second wicking member, wherein the absorbent member is disposed between the first wicking member and the second wicking member.

6. An inline storage-and-liquid-processing pouch for use with body fluids from a patient, the inline storage-and-liquid-processing pouch comprising:
   a pouch body having an interior portion divided into two parts by a first high-moisture-vapor-transfer-rate member to form a first chamber and a second chamber;
   a first port formed on the pouch body and fluidly coupled to the first chamber;
   a second port formed on the pouch body and fluidly coupled to the first chamber;
   a first evaporation port formed on the pouch body and fluidly coupled to the second chamber; and
   a second evaporation port formed on the pouch body and fluidly coupled to the second chamber.

7. The inline storage-and-liquid-processing pouch of claim 6, further comprising a storage material.

8. The inline storage-and-liquid-processing pouch of claim 7, wherein the storage material comprises an absorbent member and a first wicking member.

9. The inline storage-and-liquid-processing pouch of claim 7, wherein the storage material comprises an absorbent member, a first wicking member, and a second wicking member, wherein the absorbent member is disposed between the first wicking member and the second wicking member.

10. The inline storage-and-liquid-processing pouch of claim 6, further comprising a first micro-pump coupled to the pouch body and fluidly coupled to the first port, wherein the first micro-pump is operable to produce reduced pressure delivered to the first port.

11. The inline storage-and-liquid-processing pouch of claim 6, further comprising a second micro-pump coupled to the pouch body and fluidly coupled to the first evaporation port, wherein the second micro-pump is operable to produce air flow in the second chamber between the first evaporation port and the second evaporation port.

12. The inline storage-and-liquid-processing pouch of claim 6, further comprising:
   a first micro-pump coupled to the pouch body and fluidly coupled to the first port, wherein the first micro-pump is operable to produce reduced pressure that is delivered to the first port; and
   a second micro-pump coupled to the pouch body and fluidly coupled to the first evaporation port, wherein the second micro-pump is operable to produce air flow in the second chamber between the first evaporation port and the second evaporation port.

13. The inline storage-and-liquid-processing pouch of claim 6, wherein the pouch body has surface area in plane view greater than 200 centimeters$^2$ and less than 730 centimeters$^2$.

14. An inline storage-and-liquid-processing pouch for use with body fluids from a patient, the inline storage-and-liquid-processing pouch comprising:
   a pouch body having an interior portion divided into three parts by a first high-moisture-vapor-transfer-rate member and a second high-moisture-vapor-transfer-rate member to form a first chamber, a second chamber, and a third chamber, wherein the first chamber is between the second and third chambers;
   a first air-movement manifold disposed within the second chamber;
   a second air-movement manifold disposed within the second chamber;
   a first port formed on the pouch body and fluidly coupled to the first chamber;
   a second port formed on the pouch body and fluidly coupled to the first chamber;
   a first evaporation port formed on the pouch body and fluidly coupled to the second chamber;
   a second evaporation port formed on the pouch body and fluidly coupled to the second chamber;
   a third evaporation port formed on the pouch body and fluidly coupled to the third chamber; and
   a fourth evaporation port formed on the pouch body and fluidly coupled to the third chamber.

15. The inline storage-and-liquid-processing pouch of claim 14, further comprising a storage material disposed within the first chamber.

16. The inline storage-and-liquid-processing pouch of claim 15, wherein the storage material comprises an absorbent member and a first wicking member.

17. The inline storage-and-liquid-processing pouch of claim 15, wherein the storage material comprises an absorbent member, a first wicking member, and a second wicking member, wherein the absorbent member is disposed between the first wicking member and the second wicking member.

18. The system of claim 1, further comprising a reduced-pressure source fluidly coupled to the first chamber.

19. The system of claim 1, wherein the positive-pressure source is fluidly coupled to the second chamber at a second evaporation port and configured to move air within the second chamber.

20. An inline storage-and-liquid-processing pouch for use with body fluids from a patient, the inline storage-and-liquid-processing pouch comprising:
   a pouch body having an interior portion comprising a first chamber and a second chamber;
   a storage material disposed within the first chamber;
   an air-movement manifold disposed within the second chamber;
   a first port adapted to fluidly couple the first chamber to a reduced-pressure source; and
   a second port adapted to fluidly couple the second chamber to a positive-pressure source.

21. The inline storage-and-liquid-processing pouch of claim 20, wherein the pouch body is adapted to maintain a relative humidity gradient between the first chamber and the second chamber.

22. The inline storage-and-liquid-processing pouch of claim 20, wherein the storage material comprises an absorbent member and a first wicking member.

* * * * *

UNITED STATES PATENT AND TRADEMARK OFFICE
CERTIFICATE OF CORRECTION

| | | |
|---|---|---|
| PATENT NO. | : 9,877,873 B2 | Page 1 of 1 |
| APPLICATION NO. | : 14/860165 | |
| DATED | : January 30, 2018 | |
| INVENTOR(S) | : Richard Daniel John Coulthard et al. | |

It is certified that error appears in the above-identified patent and that said Letters Patent is hereby corrected as shown below:

In the Claims

At Column 12, Claim number 14, Line 7, delete "second chamber" and replace with "third chamber"

Signed and Sealed this
Eleventh Day of September, 2018

Andrei Iancu
*Director of the United States Patent and Trademark Office*